US008399632B2

(12) United States Patent
Mitterer et al.

(10) Patent No.: US 8,399,632 B2
(45) Date of Patent: Mar. 19, 2013

(54) METHOD FOR THE PURIFICATION OF RECOMBINANT BLOOD COAGULATION FACTOR IX ENRICHED IN SULFATED AND/OR PHOSPHORYLATED MOLECULES

(75) Inventors: Artur Mitterer, Orth/Donau (AT); Meinhard Hasslacher, Vienna (AT); Christian Fiedler, Vienna (AT)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 464 days.

(21) Appl. No.: 12/037,735

(22) Filed: Feb. 26, 2008

(65) Prior Publication Data
US 2008/0207879 A1 Aug. 28, 2008

Related U.S. Application Data

(60) Provisional application No. 60/904,009, filed on Feb. 28, 2007.

(51) Int. Cl.
*C07K 1/18* (2006.01)
*C07K 14/745* (2006.01)
(52) U.S. Cl. .................................. 530/416; 530/384
(58) Field of Classification Search .................. None
See application file for complete search history.

(56) References Cited

U.S. PATENT DOCUMENTS
5,714,583 A 2/1998 Foster et al.

FOREIGN PATENT DOCUMENTS
| EP | 0 363 126 A2 | 4/1990 |
| EP | 0 363 126 A3 | 4/1990 |
| WO | WO 96/40883 A1 | 12/1996 |
| WO | WO 2007/101681 A1 | 9/2007 |

OTHER PUBLICATIONS

Williams, A., et al. 1998 Current Protocols in Molecular Biology 44(10.10): 1-30.*
Griffith, M.J. et al., "N-Glycan Sialylation is Important for In Vivo Recovery of Recombinant Factor IX," *Journal of Thrombosis and Haemostasis Abstracts From XXIst ISTH Congress*, Aug. 2007, vol. 5, Supplement 1, 1 page.
Josic, D. et al., "Preparation of Vitamin K-Dependent Proteins, Such as Clotting Factors II, VII, IX and X and Clotting Inhibitor Protein C," *Journal of Chromatography B*, 2003, vol. 790, pp. 183-197.
Arruda, V.R. et al., "Posttranslational Modifications of Recombinant Myotube-Synthesized Human Factor IX," *Blood*, Jan. 1, 2001, vol. 97, No. 1, pp. 130-138.
Autin, L. et al., "Molecular Models of the Procoagulant Factor Villa-Factor IXa Complex," *Journal of Thrombosis and Haemostasis*, 2005, vol. 3, pp. 2044-2056.
Björkman, S. et al., "Pharmacokinetics of Recombinant Factor IX in Relation to Age of the Patient: Implications for Dosing in Prophylaxis," *Haemophilia*, 2001, vol. 7, pp. 133-139.
Bond, M. et al., "Biochemical Characterization of Recombinant Factor IX," *Seminars in Hematology*, Apr. 1998, vol. 35, No. 2, Suppl. 2, pp. 11-17.
Brinkhous, K.M. et al., "Recombinant Human Factor IX: Replacement Therapy, Prophylaxis, and Pharmacokinetics in Canine Hemophilia B," *Blood*, Oct. 1, 1996, vol. 88, No. 7, pp. 2603-2610.
Choo, K.H. et al., "Molecular Cloning of the Gene for Human Anti-Haemophillic Factor IX," *Nature*, Sep. 9, 1982, vol. 299, pp. 178-180.
Ewenstein, B.M. et al., "Pharmacokinetic Analysis of Plasma-Derived and Recombinant FIX Concentrates in Previously Treated Patients With Moderate or Severe Hemophilia B," *Transfusion*, Feb. 2002, vol. 42, pp. 190-197.
Harrison, S. et al., "The Manufacturing Process for Recombinant Factor IX," *Seminars in Hematology*, Apr. 1998, vol. 35, No. 2, Suppl. 2, pp. 4-10.
Jaye, M. et al., "Isolation of a Human Anti-Haemophillic Factor IX cDNA Clone Using a Unique 52-Base Synthetic Oligonucleotide Probe Deduced From the Amino Acid sequence of Bovine Factor IX," *Nucleic Acid Research*, 1983, vol. 11, No. 8, pp. 2325-2335.
Kaufman, R.J. et al., "Expression, Purification, and Characterization of Recombinant γ-Carboxylated Factor IX Synthesized in Chinese Hamster Ovary Cells," *The Journal of Biological Chemistry*, Jul. 25, 1986, vol. 261, No. 21, pp. 9622-9628.
Kaufman, R.J., "Post-Translational Modifications Required for Coagulation Factor Secretion and Function," *Thrombosis and Haemostasis*, 1998, vol. 79, pp. 1068-1079.
Keith, J.C., Jr., et al., "Evaluation of Recombinant Human Factor IX: Pharmacokinetic Studies in the Rat and the Dog," *Thrombosis and Haemostasis*, 1994, vol. 73, No. 1, pp. 101-105.
Kisker, C.T. et al., "Prophylaxis in Factor IX Deficiency Product and Patient Variation," *Haemophilia*, 2003, vol. 9, pp. 279-284.
Kurachi, K. et al., "Isolation and Characterization of a cDNA Coding for Human Factor IX," *Proc. Natl. Acad. Sci. USA*, Nov. 1982, vol. 79, pp. 6461-6464.
Mammalian Gene Collection Program Team at al., "Generation and Initial Analysis of More Than 15,000 Full-Length Human and Mouse cDNA Sequences," *PNAS*, Dec. 24, 2002, vol. 99, No. 26, pp. 16899-16903.
McCarthy, K. et al., "Pharmacokinetics of Recombinant Factor IX After Intravenous and Subcutaneous Administration in Dogs and Cynomolgus Monkeys," *Thrombosis and Haemostasis*, 2002, vol. 87, pp. 824-830.
McGraw, R.A. et al., "Evidence for a Prevalent Dimorphism in the Activation Peptide of Human Coagulation factor IX," *Proc. Natl. Acad. Sci. USA*, May 1985, vol. 82, pp. 2847-2851.
Poon, M-C. et at., "Recombinant Factor IX Recovery and Inhibitor Safety: A Canadian Post-Licensure Surveillance Study," *Thrombosis and Haemostasis*, 2002, vol. 87, pp. 431-435.
Ragni, M.V. et al., "Use of Recombinant Factor IX in Subjects With Haemophilia B Undergoing Surgery," *Haemophilia*, 2002, vol. 8, pp. 91-97.
Roth, D.A. et al., "Human Recombinant Factor IX: Safety and Efficacy studies in Hemophilia B Patients Previously Treated With Plasma-Derived Factor IX Concentrates," *Blood*, Dec. 15, 2001, vol. 98, No. 13, pp. 3600-3606.

(Continued)

*Primary Examiner* — Marsha Tsay
(74) *Attorney, Agent, or Firm* — Morgan, Lewis & Bockius LLP

(57) ABSTRACT

The present invention relates to a method for the purification of rFIX using anion exchange chromatography in the pseudo-affinity mode, wherein said method comprises a wash step with a wash buffer having a salt concentration of more than 200 mM. The purification according to the invention provides a method to enrich rFIX molecules which have been post-translationally modified by sulfation and/or phosphorylation. The present invention further relates to purified rFIX compositions enriched in monosulfated and/or monophosphorylated rFIX molecules.

19 Claims, No Drawings

OTHER PUBLICATIONS

Schaub, R. et al., "Preclinical Studies of Recombinant Factor IX," *Seminars in Hematology*, Apr. 1998, vol. 35, No. 2, Suppl. 2, pp. 28-32.

Shapiro, A.D. et al., "The Safety and Efficacy of Recombinant Human Blood Coagulation Factor IX in Previously Untreated Patients With severe or Moderatley Severe Hemophilia B," *Blood*, Jan. 15, 2005, vol. 105, No. 2, pp. 518-525.

Wasley, L.C. et al., "PACE/Furin Can Process the Vitamin K-Dependent Pro-Factor IX Precursor Within the Secretory Pathway," *The Journal of Biological Chemistry*, Apr. 25, 1993, vol. 268, No. 12, pp. 8458-8465.

White, G.C., II, et al., "Recombinant Factor IX," *Thrombosis and Haemostasis*, 1997, vol. 78, No. 1, pp. 261-265.

White, G.C., II., et al., "Mammalian Recombinant Coagulation Proteins: Structure and Function," *Transfus. Sci.*, 1998, vol. 19, No. 2, pp. 177-189.

\* cited by examiner

METHOD FOR THE PURIFICATION OF RECOMBINANT BLOOD COAGULATION FACTOR IX ENRICHED IN SULFATED AND/OR PHOSPHORYLATED MOLECULES

CROSS REFERENCE TO RELATED APPLICATIONS

The present application claims priority to U.S. Ser. No. 60/904,009, filed Feb. 28, 2007, herein incorporated by reference in its entirety.

FIELD OF THE INVENTION

The present invention relates to a method for the purification of recombinant blood coagulation factor IX (rFIX) by anion exchange chromatography, wherein the method comprises a wash step with a wash buffer which has a salt concentration of more than 200 mM. Furthermore, the invention relates to compositions enriched in rFIX molecules which have been posttranslationally modified by sulfation and/or phosphorylation.

BACKGROUND OF THE INVENTION

Vitamin K-dependent proteins are a class of proteins involved in maintaining hemostasis. The dependency on vitamin K occurs during the biosynthesis of the proteins, as vitamin K is a cofactor in the carboxylation of glutamic acid residues of the proteins. The result of this reaction is the formation of a γ-carboxyglutamate (gamma-carboxyglutamate), referred to as gla residue. The formation of gla residues within several proteins of the blood clotting cascade is critical for their normal function. The presence of gla residues allows the protein to chelate divalent cations, e.g. calcium, and thereby render an altered conformation, an alteration of the surface charges on the protein, and thus, an alteration of the biological activity of the protein.

EP0363126 utilizes said changes in the protein in the presence of divalent cations to selectively purify recombinant vitamin K-dependent proteins. The method is based on conventional ion exchange chromatography to separate the vitamin K-dependent proteins based on the ionically altered binding affinity to the substrate in the absence or presence of divalent cations and is called "pseudo-affinity chromatography". Thus, the method described in EP0363126 allows to select recombinant vitamin K-dependent proteins based on their quantity of gla residues.

U.S. Pat. No. 5,714,583 describes purification methods for rFIX using anion exchange chromatography in the pseudo-affinity mode to increase the purity of rFIX. Selected inactive forms of FIX and contaminating host cell proteins remain bound to the column, while active FIX and some less active forms are eluted by the addition of a divalent cation to the buffer.

EP0363126 as well as U.S. Pat. No. 5,714,583 are aimed on the purification of recombinant protein molecules with an increased biological activity.

However, the therapeutic efficacy depends not only on the biological activity of a recombinant protein, but also on the in vivo recovery.

This can be seen from the following example: Hemophilia B, a hereditary recessive bleeding disorder, is successfully treated by replacement therapy consisting of the administration of preparations of human plasma derived (pdFIX) or recombinant blood coagulation factor IX (rFIX). The commercially available recombinant product, which is marketed under the trade name Benefix™, is manufactured by using stable transfected Chinese hamster ovary (CHO) cells co-expressing rFIX together with endopeptidase PACE/Furin, and is highly purified via multiple filtration and chromatographic steps (Kaufman et al., 1986; Wasley et al., 1993; Harrison et al., 1998). In clinical studies, Benefix™ has been shown to be safe and effective, but a 20 to 50% higher dosage than for pdFIX is needed for successful treatment. This is due to a 30 to 50% lower in vivo recovery for CHO derived rFIX than for pdFIX, as revealed by pharmacokinetic data collected from pre-clinical and clinical studies, where pdFIX and rFIX are compared in different animal models (Keith, Jr. et al., 1995; Brinkhous et al., 1996; Schaub et al., 1998; McCarthy et al., 2002), and clinical studies in hemophilia B patients (Keith, Jr. et al., 1995; White et al., 1997; White et al., 1998; Bjorkman et al., 2001; Roth et al., 2001; Ewenstein et al., 2002; Poon et al., 2002; Ragni et al., 2002; Kisker et al., 2003; Shapiro et al., 2005a). The circulating half-life of rFIX is not distinguishable from pdFIX preparations. Biochemical comparison between pdFIX and CHO derived rFIX revealed differences in post-translational modifications (Bond et al., 1998). The lower degree of phosphorylation of a unique site at the activation-peptide amino acid serine 158 and the lower degree of sulfation of tyrosine 155 have been assigned to the lower in-vivo recovery of rFIX (White et al., 1997; Kaufman, 1998), although experimental evidence to proof this assumption has not been published to-date. These two modifications were identified to occur at less than 15% for the tyrosine-sulfation and at less than 1% for the serine phosphorylation in the recombinant protein, whereas the plasma derived protein has both modifications to more than 90% completed. Similar pharmacokinetic properties to Benefix™ were found for myotube-synthesized rFIX after adeno-associated viral vector mediated gene delivery in a mouse model (Arruda et al., 2001).

Post-translational modifications such as sulfation and/or phosphorylation are affected by the cell line as well as the culture conditions used in the large scale production of recombinant proteins (Kaufman, 1998).

Therefore, a strong need exists for purification methods of rFIX from cell culture supernatants which allow an enrichment of molecules which have been post-translationally modified by sulfation and/or phosphorylation. Such new purification methods would allow to provide rFIX preparations which have an improved in vivo recovery and thus, could be administered in lower doses than the preparations used in the prior art.

SUMMARY OF THE INVENTION

The present invention relates to a method for the purification of rFIX comprising the steps of loading a composition comprising a rFIX onto an anion exchange material, washing the anion exchange material using a wash buffer which has a salt concentration of more than 200 mM, eluting the rFIX from the anion exchange material using an elution buffer comprising divalent cations, and collecting the eluate. The purification according to the invention provides a method to enrich rFIX molecules which have been posttranslationally modified by sulfation and/or phosphorylation.

The present invention further relates to compositions comprising rFIX obtained by the method according to this invention. Said compositions comprise an increased relative amount of monosulfated and/or monophosphorylated rFIX molecules compared to the relative amount of monosulfated and/or monophosphorylated rFIX present in the wash fraction. In one example, said compositions comprise a relative amount of at least 20% of monosulfated and/or monophosphorylated rFIX molecules.

DETAILED DESCRIPTION OF THE INVENTION

One aspect of the present invention relates to a method for the purification of rFIX comprising the steps of
a) loading a composition comprising a rFIX onto an anion exchange material,
b) washing the anion exchange material using a wash buffer which has a salt concentration of more than 200 mM,
c) eluting the rFIX from the anion exchange material using an elution buffer comprising divalent cations, and
d) collecting the eluate.

According to the present invention, the term "recombinant FIX" does not underlie a specific restriction and may include any recombinant FIX protein, heterologous or naturally occurring, obtained via recombinant DNA technology, or a biologically active derivative thereof. In certain embodiments, the term encompasses proteins and nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity, over a region of at least about 25, 50, 100, 200, 300, 400, 450, or more amino acids (up to the full length sequence), to a polypeptide encoded by a referenced nucleic acid or an amino acid sequence described herein; (2) specifically bind to antibodies, e.g., polyclonal antibodies, raised against an immunogen comprising a referenced amino acid sequence as described herein immunogenic fragments thereof, and conservatively modified variants thereof; (3) specifically hybridize under stringent hybridization conditions to a nucleic acid encoding a referenced amino acid sequence as described herein, and conservatively modified variants thereof; (4) have a nucleic acid sequence that has greater than about 95%, greater than about 96%, 97%, 98%, 99%, or higher nucleotide sequence identity, over a region of at least about 25, 50, 100, 150, 200, 250, 500, 1000, 2000, 2500 or more nucleotides (up to the full length sequence), to a reference nucleic acid sequence as described herein. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention are recombinant molecules (e.g., heterologous and encoding the wild type sequence or a variant thereof, or non-naturally occurring). Reference polynucleotide and polypeptide sequences include, e.g., Accession Nos. NM_000133; BC109214; BC109215; J00137P M11309; and J00136 (see, e.g., Mammalian Gene Collection Program Team, PNAS USA 99:16899-16903 (2002); Autin et al., J. Thromb. Haemost. 3:2044-2056 (2005); Jaye et al., NAR 11:2325-2335 (1983); McGraw et al., PNAS 82:2847-2851 (1985) Choo et al., Nature 299:178-180 (1982); and Kurachi and Davie, PNAS 79:6461-6464 (1982)). In one embodiment, there are 2 point mutations in the Factor IX nucleic acid sequence as compared to NM_000133: position 57: CTT→CTC Leu→Leu (no amino acid change); and position 580: ACT→GCT Thr→Ala (amino acid change).

The term "recombinant" when used with reference, e.g., to a cell, or nucleic acid, protein, or vector, indicates that the cell, nucleic acid, protein or vector, has been modified by the introduction of a heterologous or non-naturally occurring nucleic acid or protein, or the alteration of a native nucleic acid or protein, or that the cell is derived from a cell so modified. Thus, for example, recombinant cells express genes that are not found within the native (non-recombinant) form of the cell, or express wild type and variant genes that are not in the native position in the genome of the cell, or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. In one example, this term refers to a nucleic acid that is not in its native position in the genome. In another example, the nucleic acid is recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein), or that it is a protein derived from a heterologous nucleic acid.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, or 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the algorithms can account for gaps and the like. Identity exists over a region that is at least about 25 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

As used herein, the term "biologically active derivative" includes any derivative of a protein, protein complex or polypeptide having substantially the same functional and/or biological properties of the rFIX such as binding properties, and/or the same structural basis, such as a peptidic backbone. Minor deletions, additions and/or substitutions of amino acids of the polypeptide sequence of the rFIX which are not altering the biological activity of said polypeptide are also included in the present application as biologically active derivatives.

The rFIX according to the present invention may be derived from any vertebrate, e.g. a mammal. In one specific example of the present invention, the rFIX is human FIX.

The rFIX according to the present invention may be produced by any method known in the art. This may include any method known in the art for the production of recombinant DNA by genetic engineering, e.g. via reverse transcription of RNA and/or amplification of DNA. Additionally, the recombinant DNA coding for the rFIX, e.g. a plasmid, may also contain a DNA sequence encoding a selectable marker for selecting the cells which have been successfully transfected with the plasmid. In an example of the present invention, the plasmid may also confer resistance to a selectable marker, e.g. to the antibiotic drug G418, by delivering a resistance gene, e.g. the neo resistance gene conferring resistance to G418.

The production of rFIX may include any method known in the art for the introduction of recombinant DNA into eukaryotic cells by transfection, e.g. via electroporation or microinjection. For example, the recombinant expression of human FIX can be achieved by introducing an expression plasmid containing the human FIX encoding DNA sequence under the control of one or more regulating sequences such as a strong promoter, into a suitable host cell line by an appropriate transfection method resulting in cells having the introduced sequences stably integrated into the genome. The calcium-phosphate co-precipitation method is an example of a transfection method which may be used according to the present invention.

The production of rFIX may also include any method known in the art for the cultivation of said transformed cells, e.g. in a continuous or batchwise manner, and the expression of the rFIX, e.g. constitutive or upon induction. In one specific example of the present invention the nucleic acid coding for the rFIX contained in the host organism of the present invention is expressed via an expression mode selected from the group consisting of induced, transient, and permanent expression. Any expression system known in the art or commercially available can be employed for the expression of a recombinant nucleic acid encoding the FIX protein, including the use of regulatory systems such as suitable, e.g. controllable, promoters, enhancers etc.

The production of rFIX may also include any method known in the art for the isolation of the protein, e.g. from the culture medium or by harvesting the transformed cells. For example, the rFIX producing cells can be identified by isolating single-cell derived populations i.e. cell clones, via dilution after transfection and optionally via addition of a selective drug to the medium. After isolation the identified cell clones may be cultivated until confluency in order to enable the measurement of the rFIX content of the cell culture supernatant by enzyme-linked immuno-sorbent assay (ELISA) technique. Additionally, rFIX secreted by the cells may be identified for example by growing the cells in the absence of any growth promoting fetal bovine serum or components thereof. Vitamin K is added at appropriate concentrations to improve the functional properties of the rFIX. In one specific example of the present invention, the supernatant is harvested 24 hours after transfection. After identification, high rFIX protein producing cell clones may for example be further propagated and/or stored via cryopreservation. In one example of the present invention, the rFIX is co-expressed with vitamin K reductase complex subunit 1 (VKORC1) and/or furin. Examples of the coexpression of FIX with VKORC1 are described in WO06/089613.

The host cell type according to the present invention may be any mammalian cell with the ability to perform the phosphorylation and/or sulfation as posttranslational modifications of rFIX. For example said mammalian cell is derived from a mammalian cell line, like for example a cell line selected from the group consisting of SkHep-, CHO-, HEK293-, and BHK-cells. In a specific example of the present invention, rFIX is expressed in HEK293-derived cells.

In one specific example of the present invention, the rFIX according to the present invention is expressed in a host cell type with the ability to perform the phosphorylation and/or sulfation as posttranslational modifications. The ability to phosphorylate and/or sulfate corresponding residues of rFIX protein expressing host cell lines may be for example analyzed by mass-spectrometric analysis of the rFIX derived from these cell lines. For example, cell clones exhibiting the ability to add phosphorus-containing groups and/or sulfur-containing groups to the synthesized rFIX molecules, may be identified by determining the percentage of phosphorylated and/or sulfated rFIX protein molecules by MS after chromatographic purification of rFIX from cell culture supernatants as described above. The conversion of collected rFIX protein preparations into peptides may be achieved, e.g. by tryptic digestion, optionally followed by an enzymatical removal of glycosidic residues. In the following, the peptides may be separated, e.g. by reversed phase HPLC, and analyzed by ESI-QTOF-MS. The degree of phosphorylated/non-phosphorylated and/or sulfated/non-sulfated peptide may be estimated by quantification of corresponding signals.

The term "phosphorylated and/or sulfated rFIX" refers to the protein molecules which are posttranslationally modified by phosphorylation and/or sulfation. The degree of phosphorylation and/or sulfation can be determined by mass spectrometry (MS), e.g., electrospray-ionization quadrupole time of flight mass spectrometry (ESI-QTOF-MS) and can be expressed, for example, in the percentage of monophosphorylated and/or monosulfated rFIX. For example, when measured with ESI-QTOF-MS, the percentage of monophosphorylated and monosulfated rFIX in a plasma derived FIX sample used as a standard is about 98%.

As used herein, the term "monosulfated and/or monophosphorylated rFIX" means that the rFIX molecule is poststranslationally modified by sulfation at tyrosine 155 and/or by phosphorylation at serine 158. Accordingly, a "monosulfated or monophosphorylated" rFIX is a rFIX molecule which is either sulfated at tyrosine 155 or phosphorylated at serine 158. A "monosulfated and monophosphorylated" rFIX is a rFIX molecule which is sulfated at tyrosine 155 as well as phosphorylated at serine 158.

For the determination of monosulfated and/or monophosphorylated molecules, the rFIX is deglycosylated and treated with trypsin (as already mentioned above). The tryptic peptides are measured by HPLC-MS (QTOF micro coupled to a HP HPLC 1100) focusing on the peptide aa146-180 with a molecular mass of appr. 3968 Da in no-modified and unglycoslyated form. This peptide carries the amino acids tyrosine 155, which is the target for sulfation, and serine 158, which is the target for phosphorylation. In total this peptide represents the activation peptide that is removed from FIX during activation. Sulfated and/or phosphorylated forms of this peptide have a shift in the molecular mass of 80 Da leading to a peptide mass of the mono-modified form of appr. 4048 Da (mono-sulfated or mono-phosphorylated) or a peptide mass of the di-modified form of appr. 4128 Da (mono-sulfated and mono-phosphorylated). By conventional mass spectroscopy one cannot distinguish between mass increase caused by sulfation or phosphorylation which would require a high resolution method and equipment.

There is no particular limitation to the media, reagents and conditions used for culturing the cells. The cells can be cultured in a continuous or batchwise manner. In one example of the present invention the cells are cultured under serum-free or serum- and protein-free conditions. In a further example of the present invention conditions are employed under which cells that contain a recombinant nucleic acid coding for rFIX are selectively proliferated, e.g. by using a selective medium.

The term "composition comprising a rFIX" as used herein may be a supernatant of a cell culture as described above. The supernatant may be obtained by centrifugation of the cell culture medium. In another embodiment, said cell culture supernatant may be pre-purified by at least one additional purification step, e.g. filtration, ultra-diafiltration, membrane filtration, depth filtration, precipitation, cross-flow microfiltration, hollow fiber microfiltration, expanded bed adsorption (EBA) capture. EBA capture does not require cell removal prior to the capture step.

Said composition comprising a rFIX may have a salt concentration of 80 to 200 mM. In an embodiment, the concentration of said salt in the composition comprising a rFIX is 110 to 170 mM, in a further example 120 to 160 mM, and in still another example 150 mM.

As used herein, the term "salt" includes, for example, sodium salts (e.g. sodium chloride, sodium sulfate, sodium phosphate), or potassium salts (e.g. potassium chloride, potassium sulfate, potassium phosphate). All given salt concentrations refer to salts having monovalent anions (e.g. chloride salts), if not otherwise stated. If salts with polyvalent anions are used (e.g. sulfate or phosphate), the salt concentration should be respectively lower. Furthermore, the given salt concentrations refer to a buffer comprising 20 mM Tris and having a pH of 7.4. If other buffering agents and or other concentrations are used, the salt concentration has to be adapted accordingly. If, for example, the buffer is a Tris/HCl buffer system with a higher Tris concentration (and thus, higher HCl concentration), the concentration of the Cl$^-$ anions already present might reduce the concentration of the salt (e.g. NaCl) added to the wash buffer. The more ions, especially anions, are already present in the buffer, the less salt is needed.

In an embodiment, said composition comprising a rFIX has a conductivity of 9 to 20 mS/cm at 25° C. In another embodiment, said composition comprising a rFIX has a conductivity of 11 to 18 mS/cm at 25° C.; and in still another embodiment, said composition comprising a rFIX has a conductivity of 12 to 16 mS/cm at 25° C.

The conductivity referred to in the present invention can be measured, for example, by using a state-of-the-art conductivity meter (e.g. from Mettler Toledo or Sartorius, with a 4-ring conductivity cell) that is equipped with a conductivity electrode, a meter and standard solutions for calibration. When applying a certain voltage, the current passing the solution is measured. Said current is proportional to the ions present in the conducting solution. The meter then gives you the conductivity of the solution in [mS/cm] either at the temperature of measurement or the meter calculates the conductivity for a certain reference temperature that is usually 25° C. using a temperature coefficient alpha of 2%.

In an example, the composition comprising rFIX has a pH of 6 to 9, in a further example 7 to 8, in still another example a pH of 7.3 to 7.5, and in yet another example a pH of 7.4.

In a further embodiment, the composition comprising a rFIX may further comprise a protease inhibitor in a concentration of 0.1-10 mM. Said protease inhibitor may be added to the cell culture supernatant prior to loading.

As used herein, the term "protease inhibitor" includes e.g. benzamidine and aprotinin.

The composition comprising a rFIX may further comprise at least one chelating agent in a concentration sufficient to remove any divalent cations, e.g. 0.1 to 10 mM.

The term "chelating agent" as used herein, includes citrate, ethylene diamine, EDTA (ethylene-dinitrilo-tetraacetic acid), EGTA (ethylene-glycol-bis-N,N'-tetraacetic acid), NTA (nitrilo-triacetic acid), DTPA (diethylene-triamine-pentaacetic acid), CDTA (cyclohexylene-(1,2)-dinitrilo-tetraacetic acid), 3,6-dioxa-octamethylene-dinitrilo-tetraacetic acid, HEDTA (N-(2-hydroxyethyl)-ethylene-diamine-triacetic acid) or other acetic acid variants.

In an embodiment of the invention, the composition comprising a rFIX comprises 2 to 5 mM of a chelating agent. In another embodiment, said composition comprises 4 to 5 mM EDTA (ethylene-dinitrilo-tetraacetic acid). The chelating agent may be added to the cell culture supernatant prior to loading.

In one embodiment, the composition comprising a rFIX may be diluted with a dilution buffer prior to application to the column. Said dilution buffer may comprise a buffering agent (e.g. Tris, HEPES, Imidazole, Histidine, Phosphate, MOPS). Furthermore, said dilution buffer may comprise a salt in a concentration of 80 to 200 mM. In one example, the dilution buffer comprises a salt in a concentration of 120 to 160 mM. The composition comprising rFIX has a pH of 6 to 9, in a further example 7 to 8, in still another example a pH of 7.3 to 7.5, and in yet another example a pH of 7.4. The dilution buffer may further comprise a chelating agent in a concentration of 0.1-10 mM (e.g. 2 mM), and optionally a protease inhibitor in a concentration of 0.1-10 mM. In one example, the composition comprising a rFIX is diluted with 0.33 volumes of the dilution buffer (related to the volume of the load solution, i.e. the composition comprising rFIX which is to be loaded onto the anion exchange material).

The composition comprising a rFIX may be loaded onto an anion exchange column at a protein density of 0.1-50 mg FIX antigen/ml resin. In an embodiment of the invention, the composition comprising a rFIX is loaded onto the anion exchange column with 100 CVs.

Suitable anion exchange materials include resins having a positively charged group at a neutral pH, such as diethylaminoethane (DEAE), polyethyleneimine (PEI), and quaternary aminoethane (QAE) and include Q-Sepharose Fast Flow, DEAE-Sepharose Fast Flow, POROS-Q, DEAE-Toyopearl, QAE-Toyopearl, Fractogel TMAE, Fractogel-DMAE, Fractogel EMD TMAE, Matrex Cellufine DEAE and the like. In an embodiment, the anion exchange material is a tentacle-type resin as described for example in EP 0337144. In one example, the anion exchange material is Fractogel EMD TMAE 650.

Columns, bed volumes and flow rates useful in the present invention depend on the scale (Lab scale, Pilot or Commercial scale), the resin, and the hardware. Maximum flow rates can be obtained from the manufacturer of the resins.

According to the present invention, said anion exchange materials are used in the pseudo-affinity mode as described, e.g. in EP363126 and U.S. Pat. No. 5,714,583.

In another embodiment, the method of the present invention further comprises an equilibration step prior to loading of the composition comprising a rFIX onto an anion exchange material. The equilibration buffer used in said equilibration step may comprise a neutral buffer (e.g. Tris, pH 7.4) and may comprise a salt in a concentration of 80 to 200 mM. In an embodiment, the equilibration buffer comprises a salt in a concentration of 120 to 160 mM, in another embodiment in a concentration of 150 mM. The equilibration buffer may further comprise a chelating agent in a concentration of 0.1 to 10 mM (e.g. 2 mM), and/or a protease inhibitor in a concentration of 0.1 to 10 mM. The equilibration buffer may further comprise a nonionic surfactant, such as e.g. polyethylene glycol p-(1,1,3,3-tetramethylbutyl)-phenyl ether (Triton® X-100), e.g. in a concentration of 0.01 to 0.1%. The equilibration step may be conducted with a volume of 1 to 100 CVs, e.g. with 2, 4 or 5 CVs. The equilibration buffer may have a conductivity of 0.5 to 12 mS/cm at 25° C. In an example, it has a conductivity of 1 to 8 mS/cm at 25° C. In another example, the conductivity of the equilibration buffer is 2.11 mS/cm at 25° C. The conductivity of the equilibration buffer should not exceed the conductivity of the load buffer. In an embodiment of the invention, the equilibration buffer comprises 20 mM Tris, 2 mM EDTA, and 0.1% Triton X-100, and the equilibration buffer has a pH of 7.4 and a conductivity of 2.11 mS/cm at 25° C.

The treatment of the chromatography column with said equilibration buffer can be repeated at least once after the load step or any subsequent chromatography step as a re-equilibration. In one embodiment, such a re-equilibration is conducted subsequent to the load step, and/or any wash step.

The anion exchange material loaded with the composition comprising a rFIX can be washed using a wash buffer which has a salt concentration of more than 200 mM (High Salt Wash Buffer). Said High Salt Wash Buffer may comprise a salt (e.g. sodium chloride) in a concentration of 201 to 220 mM. In an example, the High Salt Wash Buffer comprises 220 mM sodium chloride. Said High Salt Wash Buffer may further comprise a buffering agent (e.g. Tris) in a concentration of 2-100 mM. In one embodiment, the High Salt Wash Buffer comprises a buffering agent in a concentration of 20-50 mM. The High Salt Wash Buffer may have a pH of 6 to 9. In an example, said High Salt Wash Buffer has a pH of 7 to 8; in another example said High Salt Wash Buffer has a pH of 7.3 to 7.5; and in still another example said High Salt Wash Buffer has a pH of 7.4.

In a further embodiment, said High Salt Wash Buffer may comprise at least one protease inhibitor in a concentration of 0.1 to 10 mM.

In still another embodiment, said High Salt Wash Buffer may further comprise at least one chelating agent in a concentration sufficient to remove any divalent cations. In one embodiment, said High Salt Wash Buffer comprises 0.1 to 10 mM of a chelating agent. In another embodiment, said High Salt Wash Buffer comprises 1 to 2 mM of a chelating agent, e.g. EDTA.

The High Salt Wash Buffer may further comprise a nonionic surfactant, such as e.g. polyethylene glycol p-(1,1,3,3-tetramethylbutyl)-phenyl ether (Triton® X-100), e.g. in a concentration of 0.01 to 0.1%.

In another embodiment, said High Salt Wash Buffer has a conductivity of 15 to 24 mS/cm at 25° C. In still another embodiment, said High Salt Wash Buffer has a conductivity of 19 to 22±1 mS/cm at 25° C.; and in yet another embodiment, said High Salt Wash Buffer has a conductivity of at least 21 mS/cm at 25° C. In an example, the High Salt Wash Buffer has a conductivity of 21±1 mS/cm at 25° C. In another example, the High Salt Wash Buffer has a conductivity of 22±1 mS/cm at 25° C.

The High Salt Wash Buffer may be applied onto the anion exchange column with a volume of 1 to 100 column volumes (CVs). In one example, said High Salt Wash Buffer is applied onto the anion exchange column with a volume of 10-25 CVs; in another example said High Salt Wash Buffer is applied onto the anion exchange column with a volume of 16±2 CVs, in still another example said High Salt Wash Buffer is applied onto the anion exchange column with a volume of 20±2 CVs.

In one example of the invention, the High Salt Wash Buffer comprises 20 mM Tris, 220 mM sodium chloride, 1 mM EDTA and has a pH of 7.4 and a conductivity of 21 mS/cm at 25° C.

In another example of the invention, the High Salt Wash Buffer fraction is collected after having passed the anion exchange material.

The term "High Salt Wash Buffer fraction" as used herein refers to the High Salt Wash Buffer which has been collected after having passed the anion exchange material. The content of monosulfated and/or monophosphorylated rFIX molecules of said High Salt Wash Buffer fraction can be determined as described above. The amount of monosulfated and/or monophosphorylated rFIX molecules of said High Salt Wash Buffer fraction may be compared to the amount of monosulfated and/or monophosphorylated rFIX present in the composition comprising rFIX and/or the purified composition comprising rFIX.

Said wash step using a High Salt Wash Buffer may be conducted after the loading of the column, either subsequent to the loading or after additional steps.

In an embodiment, the above described wash step with a High Salt Wash Buffer can be repeated at least once.

In another embodiment, the method optionally comprises at least one additional wash step using a wash buffer (e.g. Tris buffer, pH 7.4) which has a salt concentration lower than the High Salt Wash Buffer (Lower Salt Wash Buffer).

In an example, said Lower Salt Wash Buffer comprises a salt (e.g. sodium chloride) in a concentration of 200 mM. In another example, the High Salt Wash Buffer comprises a salt (e.g. sodium chloride) in a concentration of 220 mM and the Lower Salt Wash Buffer comprises a salt (e.g. sodium chloride) in a concentration of 200 mM. In one example, the Lower Salt Wash Buffer has a conductivity of 20±1 mS/cm at 25° C. Said Lower Salt Wash Buffer may further comprise at least one chelating agent and/or at least one protease inhibitor. Said wash step using the Lower Salt Wash Buffer may be conducted with a volume of 1 to 100 CVs, e.g. 5 to 10 CVs. Specific examples of said Lower Salt Wash Buffer, the buffering agents and their concentration, the pH, the column volumes and concentrations of further buffer components (e.g. chelating agents, protease inhibitors) are corresponding to the examples and embodiments of the High Salt Wash Buffer (as described above). According to the method of the invention, said additional wash step using the Lower Salt Wash Buffer may be conducted prior or subsequent to the wash step with the High Salt Wash Buffer. In one embodiment, the at least one optional wash step using the Lower Salt Wash Buffer may be conducted between steps a) and b) of the method as claimed in claim 1.

In an embodiment, said Lower Salt Wash Buffer has a conductivity equal to or higher than the loaded composition comprising a rFIX, lower than the wash step with the High Salt Wash Buffer, and higher than the elution buffer.

Following the at least one wash step, a conditioning step may be conducted. Such a conditioning step should be conducted especially in preparation of a gradient elution as specified below. Thus, in an embodiment of the invention, the conditioning step is conducted with the one of the two gradient elution buffers having the lower conductivity (Gradient Buffer A). For said conditioning step, 1 to 10 CVs of the gradient buffer as described above (e.g. Gradient Buffer A) may be applied onto the column. In an example, the conditioning step is conducted with a volume of 1 to 4 CVs, in still another example with 2 CVs.

The method of the present invention further comprises a step of eluting the rFIX from the anion exchange material using an elution buffer comprising divalent cations, e.g. $Ca^{2+}$. For example, said elution buffer may comprise a calcium salt (e.g. $CaCl_2$) in an amount of 0.5 to 10 mM. In one example, said elution buffer may comprise a calcium salt in an amount of 2 to 5 mM. Other useful divalent cations may be selected from the group consisting of magnesium, manganese, strontium, zinc, cobalt, and nickel. Useful salts are e.g. chloride salts ($MgCl_2$, $CaCl_2$, $SrCl_2$, $ZnCl_2$, $CoCl_2$, $NiCl_2$), or acetate salts, such as e.g. $Mg(CH_3COO)_2$, $Ca(CH_3COO)_2$, $Sr(CH_3COO)_2$, $Zn(CH_3COO)_2$, $Co(CH_3COO)_2$, $Ni(CH_3COO)_2$).

The elution of the product (i.e. the dissociation of the rFIX from the anion exchange resin) is effected by the addition of said divalent cations. Therefore, the conductivity of the elution buffer is not the key condition for elution. Thus, the conductivity of the elution buffer can be lower than the conductivity of the wash steps.

In an example, the elution buffer comprises a buffering agent (e.g. Tris, HEPES, Imidazole, Histidine, Phosphate, MOPS) in a concentration of 2-100 mM. In one example, the elution buffer comprises a buffering agent in a concentration of 20-50 mM.

The elution buffer may have a pH of 6 to 9. In one embodiment, the elution buffer has a pH of 7 to 8, in another embodiment a pH of 7.3-7.5, and in still another embodiment a pH of 7.4

The elution buffer may further comprise a salt, such as chloride salts (e.g. sodium chloride or potassium chloride). Said chloride salt can be present in an amount of 80-200 mM. In an example, the elution buffer comprises a chloride salt in a concentration of 150-190 mM, in another example the elution buffer comprises a chloride salt in a concentration of 180 mM.

In one embodiment of the invention, the elution buffer may comprise a protease inhibitor in a concentration of 0.1-10 mM.

The elution buffer may further comprise a nonionic surfactant, such as e.g. polyethylene glycol p-(1,1,3,3-tetramethylbutyl)-phenyl ether (Triton® X-100).

In another embodiment, the elution buffer may have a conductivity of 10-20 mS/cm at 25° C., in another embodiment it has a conductivity in the range of 15-19 mS/cm at 25° C., and in still another embodiment it has a conductivity of 18±1 mS/cm at 25° C. In an example, the elution buffer may have a conductivity of at least 10 mS/cm at 25° C.

Elution may be conducted with a volume of 2-50 CVs. In one embodiment, elution is conducted with a volume of 3-5 CVs. In another embodiment, elution is conducted with a volume of 3 CVs.

In one embodiment of the present invention, the elution buffer comprises 20 mM Tris, 180 mM sodium chloride, 2 to 5 mM $CaCl_2$, and has a pH of 7.4, and has a conductivity of 18±1 mS/cm at 25° C.

In one embodiment of the present invention, the elution buffer has a lower conductivity than the High Salt Wash Buffer. In another embodiment, the elution buffer has a lower conductivity than the Lower Salt Wash Buffer. In still another embodiment, the elution buffer has a higher conductivity than the composition comprising a rFIX loaded onto the anion exchange column (load solution). In another example, the elution buffer has a higher conductivity than the load solution, and the elution buffer has a lower conductivity than the High Salt Wash Buffer. In still another example, the elution buffer has a higher conductivity than the load solution, and the elution buffer has a lower conductivity than the Lower Salt Wash Buffer, and the Lower Salt Wash Buffer has a lower conductivity than the High Salt Wash Buffer.

In another embodiment of the invention, the elution is conducted with a gradient of two elution buffers having different conductivity. In one embodiment, the elution gradient is a linear gradient. The gradient for elution may range, for example, from 100% of Gradient Buffer A and 0% of Gradient Buffer B to 0% Gradient Buffer A and 100% of Gradient Buffer B. However, the starting composition of the gradient may also be any mixture of Gradient Buffer A and Gradient Buffer B. The elution gradient may extend over a range of about 1 to about 100 CVs of buffer solution. In an example, the gradient elution occurs within 2 to 10 CVs, e.g. within 5 CVs.

The steepness or slope of the gradient determines the resolution of the proteins to be separated, but also the peak broadening or sharpness of the peaks. It can be controlled with the parameters conductivity of gradient buffers A and B applied and length or extension of the gradient in CV or ml.

Thus, suitable column volumes for the gradient depend on the difference of the conductivities of both gradient buffers. In general, the more difference between the conductivities of both buffers, the more column volumes should be employed to ensure an appropriate separation. A person skilled in the art can easily determine a suitable slope of the gradient, if he/she considers the conductivities of each gradient buffer and the expected conductivity at which the product elutes. The highly phosphorylated and/or sulfated FIX molecules are expected to elute at a conductivity of at least 17 mS/cm at 25° C., especially at approximately 18±1 mS/cm at 25° C.

Gradient Buffer A may comprise a buffer substance, such as e.g. Tris, divalent cations (as described above), such as e.g. $Ca^{2+}$, a nonionic surfactant, such as e.g. Triton X-100, and may have a pH of 6 to 9. In one embodiment, Gradient Buffer A has a pH of 7 to 8, in another embodiment a pH of 7.3-7.5, and in still another embodiment a pH of 7.4. In an example, Gradient Buffer A comprises a calcium salt (e.g. $CaCl_2$) in an amount of 0.5 to 10 mM, e.g. 2 mM. Furthermore, Gradient Buffer A may comprise a salt, e.g. sodium chloride. The salt concentration of Gradient Buffer A should be below the amount effecting elution of the FIX composition, e.g. about 0 to 150 mM. Gradient Buffer A may have a conductivity of 0.5 to 16 mS/cm at 25° C. In one example, Gradient Buffer A has a conductivity of 2.11 mS/cm at 25° C. The conductivity of the Gradient Buffer A should be lower than the conductivity at which the FIX composition is expected to elute.

Gradient Buffer B may comprise a buffer substance, such as e.g. Tris, divalent cations (as described above), such as e.g. $Ca^{2+}$, a nonionic surfactant, such as e.g. Triton X-100, a salt, such as e.g. sodium chloride, and may have a pH of 6 to 9. In one embodiment, Gradient Buffer B has a pH of 7 to 8, in another embodiment a pH of 7.3-7.5, and in still another embodiment a pH of 7.4. Furthermore, Gradient Buffer B may comprise a calcium salt (e.g. $CaCl_2$) in an amount of 0.5 to 10 mM, e.g. 2 mM. In an embodiment of the invention, Gradient Buffer B may comprise the salt, e.g. sodium chloride, in an amount of 150 to up to 1000 or 2000 mM. In one example, the salt concentration is 180 mM. Gradient Buffer B may have a conductivity of more than 15 mS/cm at 25° C. In one example, Gradient Buffer B has a conductivity of more than 18.6 mS/cm at 25° C. The conductivity of Gradient Buffer B may range up to 80 or 160 mS/cm at 25° C. In an example, Gradient Buffer B has the same ingredients in the same amounts as Gradient Buffer A and has also the same pH as Gradient Buffer A, except that Gradient Buffer B comprises a salt in addition (if Gradient Buffer A does not comprise a salt) or in a higher concentration than Gradient Buffer A and thus, has a higher conductivity than Gradient Buffer A.

In one example, Gradient Buffer A comprises 20 mM Tris, 2 mM $CaCl_2$, 0.1% Triton X-100 and has a pH of 7.48 and a conductivity of 2.11 mS/cm at 25° C.

In an example, Gradient Buffer B comprises 20 mM Tris, 2 mM $CaCl_2$, 180 mM sodium chloride, 0.1% Triton X-100 and has a pH of 7.40 and a conductivity of 18.6 mS/cm at 25° C.

Following the gradient elution, the elution process may be completed by applying 2 CVs of Gradient Buffer B.

Subsequent to the elution, at least one post elution step may be conducted by applying 2 CVs of a Post Elution Buffer. The Post Elution Buffer may comprise a buffer substance, such as e.g. Tris, a nonionic surfactant, such as e.g. Triton X-100, a salt, such as e.g. sodium chloride, and may have a pH of 6 to 9. The Post Elution Buffer should have a conductivity greater than Gradient Buffer B, which can range to up to 80 or 160 mS/cm at 25° C. In an embodiment of the invention, the Post Elution Buffer has a conductivity of 37.7 mS/cm at 25° C. Furthermore, the Post Elution Buffer may comprise the salt, e.g. sodium chloride, in an amount greater than the Gradient Buffer B, which may range to up to 1000 or 2000 mM. In one example, the Post Elution Buffer has a salt concentration of 400 mM. With said post elution step, protein and other contaminants (e.g. nucleic acids) may be removed from the column. Thus, the column may be purified from such contaminants by said post elution step(s).

In an example, the Post Elution Buffer comprises 20 mM Tris, 400 mM sodium chloride, 0.1% Triton X-100, and has a pH of 7.45 and a conductivity of 37.7 mS/cm at 25° C.

The eluate is collected after having passed the anion exchange material and may be pooled according to the UV peak.

The term "eluate" as used herein refers to the elution buffer which has been collected after having passed the anion exchange material and which includes the purified composition comprising rFIX. The purified composition comprising rFIX in the eluate is bound to the divalent cation.

The eluate may be contacted with a resin that has an immobilized chelating agent to remove the divalent cation from the purified composition comprising rFIX.

Said purified composition comprising rFIX obtained by the method according to the invention may then be subjected to one or more further purification and/or concentration steps. Such further purification or concentration steps include, for example, hydrohobic interaction chromatography, anion exchange chromatography, cation exchange chromatography, affinity chromatography, size exclusion chromatography, mixed mode chromatography (e.g. Hydrophobic Charge Induction Chromatography (HCIC), and/or multimodal cation exchange chromatography), IMAC (immobilized metal affinity chromatography), and phenyl boronate affinity chromatography.

The purified composition comprising rFIX obtained by the method according to the invention may be formulated as a pharmaceutical preparation.

In an embodiment, the method according to the present invention further comprises a post elution step. The buffer used for said post elution step may comprise a neutral buffer (e.g. Tris, pH 7.4), a nonionic surfactant (such as e.g. Triton® X-100) and a chloride salt in a concentration of 500-2000 mM. In one example, the buffer used for said post elution step may comprise a chloride salt in a concentration of 1000 mM. In another example, the buffer used for said post elution step may comprise a chloride salt in a concentration of 400 mM. The buffer used for said post elution step may have a pH of 7 to 8, e.g. 7.5, and may have a conductivity of about 35 to 40 mS/cm at 25° C., e.g. 37±1 mS/cm at 25° C. The post elution step may be conducted with a volume of 1-100 CVs. For example, the post elution step may be conducted with a volume of 5 to 25 CVs. In one specific example, the post elution step may be conducted with a volume of 15 CVs.

The purified composition comprising rFIX may be analyzed by methods known in the art for analyzing recombinant proteins, e.g. the ELISA technique. In addition, the protein integrity and activity may be assessed by measuring activated partial thromboplastin time (APTT) and by electrophoresis techniques including immuno-blotting.

Examples for the detection systems of the phosphorylation and/or sulfation of rFIX are known to a person skilled in the art. For example, degrees of phosphorylation and/or sulfation can be analyzed by Liquid Chromatography with MS (LC-MS). It is within the knowledge of a person skilled in the art to choose the optimal parameters, such as buffer system, temperature and pH for the respective detection system to be used.

The improved pharmacokinetic properties of phosphorylated and/or sulfated rFIX protein molecules may be confirmed e.g. in respective knockout mouse models.

According to the present invention, the in vivo recovery of purified compositions comprising rFIX after injection into an individuum is the observed peak plasma concentration relative to the expected peak concentration based on body weight or plasma volume. It is calculated from the maximum rFIX concentration rise from baseline and is expressed as U/dL or µg/dL increase per dose (U/kg or µg/kg) injected based on bodyweight. If based on plasma volume, the in-vivo recovery can be calculated as percentage of U found per U dosed (Shapiro et al., 2005b).

The present invention further relates to a purified composition comprising rFIX obtained by a method according to this invention.

In one embodiment, the purified composition comprises an increased relative amount of monosulfated and/or monophosphorylated rFIX molecules compared to the relative amount of monosulfated and/or monophosphorylated rFIX present in the wash fractions. In one embodiment, the purified composition comprises an increased relative amount of monosulfated and/or monophosphorylated rFIX molecules compared to the relative amount of monosulfated and/or monophosphorylated rFIX present in the High Salt Wash Buffer fraction.

In another embodiment, said purified composition comprises a relative amount of monosulfated and monophosphorylated rFIX molecules which is increased at least 3 fold compared to the relative amount of monosulfated and monophosphorylated rFIX present in the High Salt Wash Buffer fraction.

Depending on the starting material, i.e. the composition comprising rFIX before purification, the method according to the present invention results in a purified composition comprising at least 20% monosulfated and/or monophosphorylated rFIX molecules related to the total amount of rFIX molecules in the purified composition. In an embodiment, said purified composition comprises a relative amount of at least 30% of monosulfated and/or monophosphorylated rFIX molecules (related to the total amount of rFIX molecules in the purified composition); in still another embodiment at least 35%; and in yet another embodiment at least 40%. In a further embodiment, said purified composition comprises a relative amount of at least 50%, 53%, 56%, 60%, 70% or 80% of monosulfated and/or monophosphorylated rFIX molecules (related to the total amount of rFIX molecules in the purified composition).

Compared to the relative amount of monosulfated and/or monophosphorylated rFIX molecules in the composition comprising rFIX before purification, the purification method of the present invention provides an enrichment in monosulfated and/or monophosphorylated rFIX molecules in the eluate of at least 10%. In one example, said enrichment is at least 20%, in still another example at least 30%.

The present invention will be further illustrated in the following examples, without any limitation thereto.

EXAMPLES

Example 1

Pharmacokinetics of De-Phosphorylated pdFIX in Comparison with pdFIX and rFIX-Product Benefix™

In order to trace altered in vivo recovery properties of FIX back to phosphorylation, the following study is performed: A pdFIX preparation is enzymatically de-phosphorylated using %-phosphatase in order to compare the pharmacokinetics of the pdFIX molecule obtained after this procedure with Benefix™ and non-de-phosphorylated pdFIX in a FIX-knockout mouse model.

Briefly, pdFIX is de-phosphorylated with λ-phosphatase and purified via anion exchange chromatography. Benefix™, de-phosphorylated pdFIX, and pdFIX are formulated in the same buffer and administered intravenously (i.v.) to FIX-knockout mice at a dosage of 200 µg/kg and a volume of 10 ml/kg. Citrated plasma samples are taken after 15 min, 30 min, 1, 2, 4, and 16 hours. Each treatment is carried out with 10 animals per treatment and time point. FIX concentrations and activities are determined via ELISA and APTT. In vivo recovery is calculated from the highest FIX concentration value found within the first hour and is expressed as percentage of the administered dose. Half-life is calculated using a one-phase least square linear regression model of logarithmic transformed ELISA or APTT values. For each treatment the median values and the 95% confidence intervals of APTT and ELISA measurements are calculated. The results are shown in Table I for in vivo recovery and in Table II for half-life. Concerning recovery, the differences of pair wise comparisons of median values from both measurement methods are significant for Benefix™ in comparison to pdFIX as well as for de-phosphorylated pdFIX to pdFIX, but not significant between Benefix™ and de-phosphorylated pdFIX. Half-life is found to be slightly higher for the rFIX product Benefix™ than for pdFIX and de-phosphorylated pdFIX.

Similar in vivo recoveries of de-phosphorylated pdFIX and rFIX are found, which are both 40 to 60% lower than the observed in vivo recovery of pdFIX. It can be concluded from this study, that at least the enzymatic removal of the phosphate group at serine 158 from the FIX activation peptide, which is the only phosphorylation site within the FIX protein, converts pdFIX into a species with an in vivo recovery comparable to CHO-derived rFIX. Therefore, phosphorylation and eventually sulfation are valid targets when aiming at the development of cell lines for the production of an improved rFIX product.

TABLE I

In vivo recovery median values (%) of rFIX product Benefix ™, pdFIX, and enzymatically de-phosphorylated pdFIX found in FIX-knockout mice and as determined by ELISA and APTT clotting assay measurements.

| Treatment | % in vivo recovery based on ELISA | | % in vivo recovery based on APTT | |
|---|---|---|---|---|
| | Median values | 95% confidence interval | Median values | 95% confidence interval |
| Benefix ™ | 7.2 | 5.4 to 9.3 | 6.0 | 5.1 to 9.0 |
| Enzymatically de-phosphorylated pdFIX | 9.5 | 8.1 to 10.8 | 8.4 | 6.9 to 11.3 |
| pdFIX | 17.0 | 13.1 to 20.0 | 15.0 | 13.6 to 20.6 |

TABLE II

Half-life median values (hours) of rFIX product Benefix ™, pdFIX, and enzymatically de-phosphorylated pdFIX found in FIX-knockout mice and as determined by ELISA and APTT clotting assay measurements.

| Treatment | Half life (hours) based on ELISA | | Half-life (hours) based on APTT | |
|---|---|---|---|---|
| | Median values | 95% confidence interval | Median values | 95% confidence interval |
| Benefix ™ | 6.5 | 5.9 to 7.2 | 8.9 | 7.9 to 12.0 |
| Enzymatically de-phosphorylated pdFIX | 6.1 | 5.7 to 6.7 | 6.7 | 6.3 to 7.4 |
| pdFIX | 5.1 | 4.5 to 5.8 | 6.6 | 6.0 to 7.6 |

Example 2

Recombinant Expression of FIX in Cell Culture and Screening for Cell Lines Exhibiting a High Degree of rFIX-Phosphorylation and Sulfation The recombinant expression of human FIX is achieved by introducing an expression plasmid containing the human FIX encoding DNA sequence under the control of a strong promoter into the host cell line by an appropriate transfection method resulting in cells having the introduced sequences stably integrated into the genome. The transfection method used is a so-called calcium-phosphate co-precipitation method. The plasmid also confers resistance to a selectable marker antibiotic drug G418 by delivering the neo resistance gene.

For the identification of rFIX-producing cells, after transfection and addition of the selective drug to the medium, the cell suspension is diluted to enable isolation of single-cell derived populations, i.e. cell clones. After isolation, these cell clones are cultivated until confluency to enable the measurement of the rFIX content of the cell culture supernatant by ELISA technique. For that purpose, the cells are grown in the absence of any growth promoting fetal bovine serum or components thereof to ensure the identification of the cells secreting rFIX. To ensure a fully functional rFIX protein, vitamin K is added at appropriate concentrations. The supernatant is harvested after 24 hours and can be analyzed by ELISA technique. In addition, the protein integrity and activity is assessed by measuring APTT and by electrophoresis techniques including immuno-blotting. High rFIX producing cell clones are further propagated and stored via cryopreservation.

To identify cell clones exhibiting the ability to add phosphor and sulfate groups to the synthesized rFIX molecules, the percentage of fully phosphorylated and sulfated rFIX is determined by mass spectrometry (MS) after chromatographic purification of rFIX from cell culture supernatants. This is accomplished by binding rFIX protein to an anion exchange column and eluting fully carboxylated rFIX via the addition of Ca(II) ions as described in EP 0669342. Thus, collected rFIX preparations are converted to peptides by tryptic digestion, and glycosidic residues are removed enzymatically. For this purpose, 2 µl trypsin solution (1 mg/ml in 0.01% trifluoracetic acid) is added to each sample and they are incubated at 37° C. for 2 hours. Then, 5 µl PNGase F (Peptide-N4-(acetyl-β-glucosaminyl)-asparagine amidase; 100 mU) is added to each sample and the mixture is incubated again at 37° C. for 18 hours. The resulting peptides are separated by reversed phase HPLC and are analyzed by ESI-QTOF-MS. A 1100 series HPLC system with a Jupiter 5µ C4 150 mm×2 mm is used. The solvents are specified below, the temperature is 40° C., and the flow is as given in the table. The entire sample volume is injected under isocratic conditions. The LCMS analysis is done using the QTOF micro coupled to the HP 1100 system having a 1:3 fused silica streamsplitter. The gradient is as given in the table.

| Solvent A: 0.1% (v/v) HCOOH in MilliQ H2O | | |
|---|---|---|
| Solvent B: 0.08% (v/v) HCOOH in acetonitril | | |
| t [min] | solvent A with % of solvent B | flow |
| 0 | 0 | 0.2 |
| 0.2 | 0 | 0.45 |
| 5.1 | 0 | 0.45 |
| 5.2 | 0 | 0.2 |
| 5.5 | 0 | 0.2 |
| 35.5 | 100 | 0.2 |
| 41.5 | 100 | 0.2 |
| 42.5 | 0 | 0.2 |
| 65.5 end of run | 0 | 0.2 |

To calculate the ion intensities and the molecular weights, the raw data are smoothed and centered.

The degree of phosphorylated and sulfated peptide is estimated by quantification of corresponding signals using the software Masslynx™ 4.0. The peaks of the several modified forms (unmodified, monosulfated or monophosphorylated, monosulfated and monophosphorylated) of FIX are extracted and the respective reconstructed ion chromatograms (RIC) are generated. The resulting peaks of said reconstructed ion chromatograms are integrated and converted into the relative peak area (%). The shoulder peaks at 25.7 min and 25.5 min are combined to one main peak area.

These techniques are used to generate cell lines producing rFIX. In this study, the recombinant expression of FIX is compared in 4 different host cell types (CHO, SkHep, BHK, HEK293) after stable transfection, and screening of appropriate producer cell lines. The percentages of phosphorylated and sulfated rFIX protein isoform from total rFIX after usual down-stream purification are assessed by LC-MS and are shown in Table III. Because of these results, HEK293 is chosen as host cell line for improved rFIX isoform screening.

A broad panel of HEK293-derived rFIX producing cell lines is generated and screened for rFIX productivity and clotting activity by the established techniques. rFIX secreted from these cell clones is prepared and analyzed according to the above outlined procedures, and exhibits at least 25% phosphorylated and sulfated isoform of total rFIX. Some examples of HEK293-derived cell clones and their characteristic rFIX cell specific productivity rates determined by ELISA and APTT are listed in Table IV. Also listed are the percentages determined by LC-MS of fully phosphorylated and sulfated FIX isoform found after chromatographic purification. As a control, the phosphorylation and sulfation content of a pdFIX product is determined by the same MS analytical procedure. The values of the CHO derived rFIX product Benefix™ taken from Kaufman et al., 1986, and Wasley et al., 1993, are also given in Table IV.

TABLE III

Comparison of percentages of phosphorylated and sulfated rFIX isoforms equally expressed in 4 different host cell types, purified from cell culture supernatants and determined by LC-MS.

| Host Cell type | Percentage of sulfated and phosphorylated rFIX isoform after usual purification | Percentage of sulfated and phosphorylated rFIX isoform after enrichment according to the present invention |
|---|---|---|
| CHO | 2-4% | not determined |
| BHK | 2% | not determined |
| SkHep | not detected | not determined |
| HEK293 | 10-20% | 25-56% |

TABLE IV

Cell specific production rates per day based on ELISA and APTT data, and percentages of fully phosphorylated and sulfated rFIX isoform produced by seven examples of HEK293-derived cell lines. The percentage of phosphorylated and sulfated FIX isoform found in pdFIX, and corresponding values of rFIX producing CHO clones taken from literature are also given.

| | μg FIX/ $10^6$ cells/day | mU FIX/ $10^6$ cells/day | Percentage of fully phosphorylated and sulfated FIX material after purification |
|---|---|---|---|
| HEK293 clone #1 | 3.2 | 50 | 25% |
| HEK293 clone #2 | 1.6 | 130 | 28% |
| HEK293 clone #3 | 2.6 | 360 | 35% |
| HEK293 clone #4 | 10 | 1200 | 53% |
| HEK293 clone #5 | 25 | 2900 | 46% |
| HEK293 clone #6 | 26 | 3300 | 49% |
| HEK293 clone #7 | 19 | 1300 | 53% |
| HEK293 clone #8 | 4.6 | 570 | 56% |
| pdFIX | — | — | 98% |
| CHO-derived cell clones; values taken from literature | 2-4 | 90-300 | <1% |

Example 3

Pharmacokinetics of Improved, HEK293-Derived rFIX in Comparison with pdFIX and rFIX Product Benefix™

The goal of the study is to confirm a significantly improved in vivo recovery but same half-life of HEK293 cell-derived rFIX in comparison to CHO cell-derived Benefix™ when administered to FIX-knockout mice. In addition, a pdFIX preparation should reveal similar pharmacokinetic properties as the HEK293-derived protein and serve as a control to show validity of the chosen animal model and to comply with literature data.

HEK293 cell lines producing high-phosphorylated and sulfated rFIX can be used for production of the test substance. rFIX can be purified from cell culture supernatants by semi-affinity calcium-dependent anion exchange chromatography (EP 0669342). Benefix™ and a pdFIX product are both commercially available. Degrees of phosphorylation and sulfation can be analyzed by LC-MS.

Briefly, rFIX and pdFIX forms can be administered i.v. in FIX-knockout mice at a dosage of 250 μg/kg and 10 ml/kg. Activity and concentration of administered FIX can be determined in plasma samples taken at multiple time points by ELISA and APTT clotting assay to calculate pharmacokinetic parameter values.

As shown in Example 2, several rFIX expressing HEK293 cell lines have been screened for performing high degrees of rFIX phosphorylation and sulfation. Frozen cells are stored in liquid nitrogen and cells can be suspended in DMEM/Ham's F12 medium containing 5-10% fetal bovine serum to larger culture systems like triple-T flasks. At confluency, the cells should be switched to vitamin K1-containing serum-free medium. Supernatants can be harvested every day for up to two weeks. rFIX can be purified via semi-affinity calcium-dependent anion exchange chromatography in an endotoxin-free system. Final product should be formulated in Benefix™ formulation buffer (10 mM L-histidine, 260 mM glycine, 1% sucrose, 0.005% Tween-80 in water, pH 6.8) at a concentration of 250 μg/10 ml and analyzed by LC-MS for degrees of phosphorylation and sulfation.

Benefix™ can be reconstituted in formulation buffer (10 mM L-histidine, 260 mM glycine, 1% sucrose, 0.005% Tween-80, pH 6.8) at a concentration of 250 μg/10 ml. The pdFIX can be reconstituted in Aqua bidest., dialyzed against Benefix™ formulation buffer and adjusted in this buffer to a concentration of 250 μg/10 ml. The pdFIX and Benefix™ should be analyzed by LC-MS for degrees of phosphorylation and sulfation.

A single dose of FIX preparations at 250 μg/kg and 10 ml/kg in Benefix™ formulation buffer can be administered via the lateral tail vein of FIX-knockout mice. Per time point and treatment, 5 male and 5 female animals should be used. Mice must be anesthetized, and blood can be collected by cardiac puncture at 15 min, 30 min, 1 hr, 4 hrs, 9 hrs post injection into sodium citrate to a final ratio of 1:10 (citrate: blood) and a final sodium citrate concentration of 3.8%. Plasma samples should be frozen immediately after centrifugation.

A control group of 5 male and 5 female mice administered with buffer only can be done at the first and the final time point.

All plasma samples can be tested for rFIX or pdFIX concentrations and activities by using ELISA and APTT clotting assay against FIX standards. Aliquots of the FIX preparations for injection should be used as reference substances to determine the actual injected amounts.

At least, the following pharmacokinetic parameters should be calculated to estimate improved pharmacokinetic properties:

e) In vivo recovery: time point with highest concentration of ELISA or APTT values compared to injected dose (U/dL or μg/dL increase per U/kg or μg/kg injected).
f) Elimination half-life (one-phase least square linear regression model of logarithmic transformed ELISA and APTT values).

Example 4

Purification of rFIX from Cell Culture Supernatant Using Step Elution

Purification Procedure:

For all experiments FIX cell culture supernatant of a transformed HEK293 cell line was used. Before application to the column the cell culture supernatant was adjusted to 10 mM EDTA and diluted with 0.33 volume of dilution buffer (20 mM Tris, 2 mM EDTA, pH=7.4) to complex free divalent cations and reduce the conductivity.

Thereafter the FIX was purified according to the procedure summarized in Table V using a 2.7 ml Fractogel EMD TMAE 650 column.

TABLE V

Chromatography schema

| Chromatography step | Volume | Buffer |
|---|---|---|
| Equilibration | about 15 CV | 20 mm Tris, 150 mM NaCl, 2 mM EDTA, pH = 7.4 |
| Loading | about 100 CV | Diluted cell culture supernatant |
| Washing | 16 CV | 20 mm Tris, 220 mM NaCl, 2 mM EDTA, pH = 7.4 |
| Elution | 3 CV | 20 mm Tris, 180 mM NaCl, 2 mM $CaCl_2$, pH = 7.4 |
| Post elution | 15 CV | 20 mm Tris, 1000 mM NaCl, pH = 7.4 |

The fraction wash and eluate pools were analyzed for sulfated/phosphorylated or non-modified FIX species by a LCMS method on a QTOF micro on deglycosylated samples (as described in Example 1). The FIX species (unmodified, monosulfated or monophosphorylated, monosulfated and monophosphorylated) were quantified by peak area integration (as described in Example 1) and the relative content of each species is summarized in Table VI. The data representing mean values of nine purification runs indicated that phosphorylated and/or sulfated FIX species are enriched in the eluate pool fraction whereas the relative content of the unmodified FIX species is reduced in the eluate pool fraction compared to the wash fraction.

TABLE VI

Analysis of FIX species by LCMS

| fraction | FIX species | Relative content [%] | Reduction/enrichment in eluate |
|---|---|---|---|
| wash | unmodified | 73.4 | — |
|  | Monosulfated or monophosphorylated | 16.3 | — |
|  | Monosulfated and monophosphorylated | 10.3 | — |
| eluate | unmodified | 40.0 | 0.54 |
|  | Monosulfated or monophosphorylated | 22.5 | 1.4 |
|  | Monosulfated and monophosphorylated | 37.5 | 3.6 |

Data represent mean values of nine experiments.

The method presented above has a potential to selectively enrich FIX molecules that are posttranslationally modified by sulfation and/or phosphorylation.

Example 5

Purification of rFIX from Cell Culture Supernatant Using Gradient Elution

For all experiments FIX cell culture supernatant of a transformed HEK293 cell line was used. Before application to the column the cell culture supernatant was adjusted to 10 mM EDTA and diluted with 0.33 volume of dilution buffer (20 mM Tris, 2 mM EDTA, pH=7.4) to complex free divalent cations and reduce the conductivity.

Thereafter the FIX was purified according to the procedure summarized in Table VII using the Anion Exchange resin QFF Sepharose. Following the gradient elution and the application of 2 CVs of Gradient Buffer B, an additional step has been conducted by applying 2 CVs of Buffer C (specified in Table VIII).

TABLE VII

Purification procedure

| | |
|---|---|
| Equilibration: | 5 CV FIX_Equilibration Buffer |
| Load: | cell culture supernatant containing 1-2 mM EDTA is loaded onto the column |
| Wash: | 20 CV FIX_Polishing_Wash Buffer |
| Re-equilibration: | 2 CV FIX_Equilibration Buffer |
| Conditioning for gradient elution: | 2 CV FIX_Gradient Buffer A |
| Gradient Elution: | 0% FIX_Gradient Buffer B/100% FIX_Gradient Buffer A to 100% FIX_Gradient Buffer B within 5 CV |
| Post Elution: | 2 CV FIX_Gradient Buffer B/2 CV FIX_Buffer C/2 CV FIX_Post Elution Buffer |

TABLE VIII

Buffers

| | |
|---|---|
| FIX_Eqilibration Buffer: | 20 mM Tris, 2 mM EDTA, 0.1% Triton X-100; pH = 7.4; conductivity 2.11 mS/cm (24.7° C.) |
| FIX_Polishing_Wash Buffer: | 20 mM Tris, 220 mM NaCl, 0.1% Triton X-100; pH = 7.46, cond.: 22.1 mS/cm (24.1° C.) |
| FIX_Gradient Buffer A: | 20 mM Tris, 2 mM $CaCl_2$, 0.1% Triton X-100; pH = 7.48, cond.: 2.11 mS/cm (24.9° C.) |
| FIX_Gradient Buffer B: | 20 mM Tris, 2 mM $CaCl_2$, 180 mM NaCl, 0.1% Triton X-100; pH = 7.40, cond.: 18.6 mS/cm (24.8° C.) |

TABLE VIII-continued

| Buffers | |
|---|---|
| FIX_Buffer C: | 20 mM Tris, 2 mM $CaCl_2$, 200 mM NaCl, 0.1% Triton X-100; pH = 7.29, cond.: 20.7 mS/cm (24.0° C.) |
| FIX_Post Elution Buffer: | 20 mM Tris, 400 mM NaCl, 0.1% Triton X-100; pH = 7.45, cond.: 37.7 mS/cm (24.3° C.) |

Results:

The fractions obtained during the gradient elution were collected into two separate pools (Pool 1-30 and Pool 31-53) and analyzed and quantified as described in Example 1 (see Table IX). The results show that FIX removed in the wash fraction has a low degree of modification (as already seen with the step elution method). In addition, the FIX eluting early from the gradient is also of low quality referring the modification grade and can be removed. The FIX material eluting late from the gradient (Pool 31-53) shows a high degree of mono-phosphorylated or mono-sulfated species as well as of mono-phosphorylated and mono-sulfated species. These results indicate that the gradient elution allows a further enrichment of the sulfated and/or phosphorylated FIX species.

TABLE IX

FIX fractions analyzed for sulfation and phosphorylation by HPLC MS method after deglycosylation by PNGase F and tryptic digest.

| Fraction name | relative content of unmodified FIX [%] | relative content of mono-phosphorylated or mono-sulfated FIX [%] | relative content of mono-phosphorylated and mono-sulfated FIX [%] |
|---|---|---|---|
| FIX Wash | 78.3 | 13.0 | 8.7 |
| FIX Eluate (Pool 1-30) | 80.0 | 20.0 | 0 |
| FIX Eluate (Pool 31-53) | 39.6 | 25.4 | 35.1 |

REFERENCES

Arruda, V. R., Hagstrom, J. N., Deitch, J., Heiman-Patterson, T., Camire, R. M., Chu, K., Fields, P. A., Herzog, R. W., Couto, L. B., Larson, P. J., and High, K. A., 2001. Post-translational modifications of recombinant myotube-synthesized human factor IX. Blood 97, 130-138.

Bjorkman, S., Shapiro, A. D., and Berntorp, E., 2001. Pharmacokinetics of recombinant factor IX in relation to age of the patient: implications for dosing in prophylaxis. Haemophilia 7, 133-139.

Bond, M., Jankowski, M., Patel, H., Karnik, S., Strang, A., Xu, B., Rouse, J., Koza, S., Letwin, B., Steckert, J., Amphleft, G., and Scoble, H., 1998. Biochemical characterization of recombinant factor IX. Semin. Hematol. 35, 11-17.

Brinkhous, K. M., Sigman, J. L., Read, M. S., Stewart, P. F., McCarthy, K. P., Timony, G. A., Leppanen, S. D., Rup, B. J., Keith, J. C., Jr., Garzone, P. D., and Schaub, R. G., 1996. Recombinant human factor IX: replacement therapy, prophylaxis, and pharmacokinetics in canine hemophilia B. Blood 88, 2603-2610.

Ewenstein, B. M., Joist, J. H., Shapiro, A. D., Hofstra, T. C., Leissinger, C. A., Seremetis, S. V., Broder, M., Mueller-Velten, G., and Schwartz, B. A., 2002. Pharmacokinetic analysis of plasma-derived and recombinant F IX concentrates in previously treated patients with moderate or severe hemophilia B. Transfusion 42, 190-197.

Franck, N., Le Seyec, J., Guguen-Guillouzo, C., and Erdtmann, L., 2005. Hepatitis C virus NS2 protein is phosphorylated by the protein kinase CK2 and targeted for degradation to the proteasome. J. Virol. 79, 2700-2708.

Harrison, S., Adamson, S., Bonam, D., Brodeur, S., Charlebois, T., Clancy, B., Costigan, R., Drapeau, D., Hamilton, M., Hanley, K., Kelley, B., Knight, A., Leonard, M., McCarthy, M., Oakes, P., Sterl, K., Switzer, M., Walsh, R., and Foster, W., 1998. The manufacturing process for recombinant factor IX. Semin. Hematol. 35, 4-10.

Herlitschka, S. E., Falkner, F. G., Schlokat, U., & Dorner, F., 1996. Overexpression of human prothrombin in permanent cell lines using a dominant selection/amplification fusion marker. *Protein Expr. Purif.,* 8, 358-364.

Kaufman, R. J., 1998. Post-translational modifications required for coagulation factor secretion and function. Thromb. Haemost. 79, 1068-1079.

Kaufman, R. J., Wasley, L. C., Furie, B. C., Furie, B., and Shoemaker, C. B., 1986. Expression, purification, and characterization of recombinant gamma-carboxylated factor IX synthesized in Chinese hamster ovary cells. J. Biol. Chem. 261, 9622-9628.

Keith, J. C., Jr., Ferranti, T. J., Misra, B., Frederick, T., Rup, B., McCarthy, K., Faulkner, R., Bush, L., and Schaub, R. G., 1995. Evaluation of recombinant human factor IX: pharmacokinetic studies in the rat and the dog. Thromb. Haemost. 73, 101-105.

Kim, Y. M., Barak, L. S., Caron, M. G., and Benovic, J. L., 2002. Regulation of arrestin-3 phosphorylation by casein kinase II. J. Biol. Chem. 277, 16837-16846.

Kisker, C. T., Eisberg, A., and Schwartz, B., 2003. Prophylaxis in factor IX deficiency product and patient variation. Haemophilia 9, 279-284.

Larson, P. J. and High, K. A., 2001. Gene therapy for hemophilia B: AAV-mediated transfer of the gene for coagulation factor IX to human muscle. Adv. Exp. Med. Biol. 489, 45-57.

Lindsay, M., Gil, G. C., Cadiz, A., Velander, W. H., Zhang, C., and Van Cott, K. E., 2004. Purification of recombinant DNA-derived factor IX produced in transgenic pig milk and fractionation of active and inactive subpopulations. J. Chromatogr. A 1026, 149-157.

Manno, C. S., 2003. The promise of third-generation recombinant therapy and gene therapy. Semin. Hematol. 40, 23-28.

McCarthy, K., Stewart, P., Sigman, J., Read, M., Keith, J. C., Jr., Brinkhous, K. M., Nichols, T. C., and Schaub, R. G., 2002. Pharmacokinetics of recombinant factor IX after intravenous and subcutaneous administration in dogs and cynomolgus monkeys. Thromb. Haemost. 87, 824-830.

McGraw, R. A., Davis, L. M., Noyes, C. M., Lundblad, R. L., Roberts, H. R., Graham, J. B., & Stafford, D. W., 1985 Evidence for a prevalent dimorphism in the activation peptide of human coagulation factor IX. Proc. Natl. Acad. Sci. U.S.A, 82, 2847-2851.

Poon, M. C., Lillicrap, D., Hensman, C., Card, R., and Scully, M. F., 2002. Recombinant factor IX recovery and inhibitor safety: a Canadian post-licensure surveillance study. Thromb. Haemost. 87, 431-435.

Ragni, M. V., Pasi, K. J., White, G. C., Giangrande, P. L., Courter, S. G., and Tubridy, K. L., 2002. Use of recombinant factor IX in subjects with haemophilia B undergoing surgery. Haemophilia. 8, 91-97.

Rost S., Fregin A., Ivaskevicius V., Conzelmann E., Hortnagel K., Pelz H. J., Lappegard K., Seifried E., Scharrer I., Tuddenham E. G., Muller C. R., Strom T. M., Oldenburg J., 2004. Mutations in VKORC1 cause warfarin resistance and multiple coagulation factor deficiency type 2. Nature February 5; 427(6974):537-41.

Roth, D. A., Kessler, C. M., Pasi, K. J., Rup, B., Courter, S. G., and Tubridy, K. L., 2001. Human recombinant factor IX: safety and efficacy studies in hemophilia B patients previously treated with plasma-derived factor IX concentrates. Blood 98, 3600-3606.

Scahill, S. J., Devos, R., Van der, H. J., & Fiers, W., 1983. Expression and characterization of the product of a human immune interferon cDNA gene in Chinese hamster ovary cells. Proc. Natl. Acad. Sci. U.S.A, 80, 4654-4658;

Schaub, R., Garzone, P., Bouchard, P., Rup, B., Keith, J., Brinkhous, K., and Larsen, G., 1998. Preclinical studies of recombinant factor IX. Semin. Hematol. 35, 28-32.

Schwaab, R. and Oldenburg, J., 2001. Gene therapy of hemophilia. Semin. Thromb. Hemost. 27, 417-424.

Shapiro, A. D., Di Paola, J., Cohen, A., Pasi, K. J., Heisel, M. A., Blanchette, V. S., Abshire, T. C., Hoots, W. K., Lusher, J. M., Negrier, C., Rothschild, C., and Roth, D. A., 2005a. The safety and efficacy of recombinant human blood coagulation factor IX in previously untreated patients with severe or moderately severe hemophilia B. Blood 105, 518-525.

Shapiro, A. D., Korth-Bradley, J., and Poon, M.-C., 2005b. Use of pharmacokinetics in the coagulation factor treatment of patients with haemophilia. Haemophilia 11, 571-582.

VandenDriessche, T., Collen, D., and Chuah, M. K., 2001. Viral vector-mediated gene therapy for hemophilia. Curr. Gene Ther. 1, 301-315.

Wasley, L. C., Rehemtulla, A., Bristol, J. A., and Kaufman, R. J., 1993. PACE/furin can process the vitamin K-dependent pro-factor IX precursor within the secretory pathway. J. Biol. Chem. 268, 8458-8465.

White, G. C., Beebe, A., and Nielsen, B., 1997. Recombinant factor IX. Thromb. Haemost. 78, 261-265.

White, G. C., Pickens, E. M., Liles, D. K., and Roberts, H. R., 1998. Mammalian recombinant coagulation proteins: structure and function. Transfus. Sci. 19, 177-189.

The invention claimed is:

1. A method for purification of a recombinant Factor IX (rFIX) composition enriched in monosulfated and/or monophosphorylated rFIX, wherein the method comprises the steps of:
   a) loading a composition comprising rFIX onto an anion exchange material;
   b) washing the anion exchange material using a high salt wash buffer having a conductivity of 22±1 mS/cm at 25° C., thereby forming a high salt wash buffer fraction comprising rFIX, wherein less than 30% of the rFIX in the high salt wash buffer fraction is monosulfated and/or monophosphorylated;
   c) eluting rFIX from the anion exchange material using a gradient of anions in an elution buffer comprising divalent cations;
   d) collecting the rFIX eluate in fractions; and
   e) pooling fractions enriched in monosulfated and/or monophosphorylated rFIX, thereby forming a purified rFIX composition enriched in monosulfated and/or monophosphorylated rFIX,
   wherein at least 30% of the rFIX in the purified rFIX composition are monosulfated and/or monophosphorylated.

2. The method according to claim 1, wherein the rFIX is human rFIX.

3. The method of claim 1, wherein the gradient is linear.

4. The method of claim 1, wherein the gradient is stepwise.

5. The method of claim 1, wherein the divalent cation is selected from the group consisting of $Ca^{2+}$, $Mg^{2+}$, $Sr^{2+}$, $Co^{2+}$, $Ni^{2+}$, and $Zn^{2+}$.

6. The method of claim 1, wherein the concentration of divalent cations is from 0.5 mM to 10 mM.

7. The method of claim 6 wherein the concentration of divalent cations is from 2 mM to 5 mM.

8. The method of claim 6, wherein the concentration of divalent cations is 2 mM.

9. The method of claim 1, wherein the elution buffer contains a buffering agent selected from the group consisting of Tris, HEPES, Imidazole, Histidine, Phosphate, and MOPS.

10. The method of claim 1, wherein at the beginning of the gradient the elution buffer has a conductivity of from 0.5 to 16 mS/cm at 25° C. and at the end of the gradient the elution buffer has a conductivity of from 80 to 160 mS/cm at 25° C.

11. The method of claim 1, wherein at the beginning of the gradient the elution buffer has a conductivity of 2.11 mS/cm at 25° C. and at the end of the gradient the elution buffer has a conductivity of more than 18.6 mS/cm at 25° C.

12. The method of claim 1, wherein at the end of the gradient, the elution buffer comprises sodium chloride in an amount from 150 mM to 2000 mM.

13. The method of claim 12, wherein at the end of the gradient, the elution buffer comprises a sodium chloride concentration of 180 mM.

14. The method of claim 1, wherein the elution buffer has a pH of from 6 to 9.

15. The method of claim 14, wherein the elution buffer has a pH of from 7 to 8.

16. The method of claim 15, wherein the elution buffer has a pH of 7.4±0.2.

17. The method of claim 1, wherein at the beginning of the gradient the elution buffer comprises 20 mM Tris, 2 mM $CaCl_2$, 0.1% Triton X-100, a pH of 7.4±0.2, and a conductivity of 2.11 mS/cm at 25° C.

18. The method of claim 1, wherein at the end of the gradient the elution buffer comprises 20 mM Tris, 2 mM $CaCl_2$, 180 mM sodium chloride, 0.1% Triton X-100, a pH of 7.4±0.2, and a conductivity of 18.6 mS/cm at 25° C.

19. The method of claim 1, wherein the anion exchange material is a resin comprising a ligand selected from the group consisting of diethylaminoethyl (DEAE), quarternary amionethyl (QAE), quarternary ammonium (Q), polyethyleneimine (PEI), triethlaminoethyl (TMAE), and dimethylaminoethyl (DMAE).

* * * * *